United States Patent
Akishika et al.

(10) Patent No.: US 12,061,140 B2
(45) Date of Patent: Aug. 13, 2024

(54) METHOD FOR EVALUATING COAL, METHOD FOR PREPARING COAL BLEND, AND METHOD FOR PRODUCING COKE

(71) Applicant: JFE STEEL CORPORATION, Tokyo (JP)

(72) Inventors: Issui Akishika, Tokyo (JP); Yusuke Dohi, Tokyo (JP); Daisuke Igawa, Tokyo (JP)

(73) Assignee: JFE STEEL CORPORATION, Tokyo (JP)

( * ) Notice: Subject to any disclaimer, the term of this patent is extended or adjusted under 35 U.S.C. 154(b) by 350 days.

(21) Appl. No.: 17/439,741

(22) PCT Filed: Mar. 5, 2020

(86) PCT No.: PCT/JP2020/009316
§ 371 (c)(1),
(2) Date: Sep. 15, 2021

(87) PCT Pub. No.: WO2020/189294
PCT Pub. Date: Sep. 24, 2020

(65) Prior Publication Data
US 2022/0170835 A1  Jun. 2, 2022

(30) Foreign Application Priority Data
Mar. 15, 2019 (JP) .................. 2019-048575

(51) Int. Cl.
*G01N 11/10* (2006.01)
*C10B 57/04* (2006.01)
(Continued)

(52) U.S. Cl.
CPC .............. *G01N 11/10* (2013.01); *C10B 57/04* (2013.01); *G01N 11/14* (2013.01); *G01N 33/24* (2013.01)

(58) Field of Classification Search
CPC .......... C10B 53/04; C10B 57/04; G01N 11/10; G01N 11/14
See application file for complete search history.

(56) References Cited

U.S. PATENT DOCUMENTS

| | | |
|---|---|---|
| 2005/0284212 A1 | 12/2005 | Marchal et al. |
| 2011/0011719 A1 | 1/2011 | Rinker |

(Continued)

FOREIGN PATENT DOCUMENTS

| | | |
|---|---|---|
| CN | 102686705 A | 9/2012 |
| CN | 103740391 A | 4/2014 |

(Continued)

OTHER PUBLICATIONS

Morotomi, H. et al. "Studies on Test for Plastic Properties of Coal by Gieseler Plastometer," Journal of the Fuel Society of Japan, vol. 53, No. 9, pp. 779-790, Jan. 1, 1974.

(Continued)

*Primary Examiner* — Renee Robinson
(74) *Attorney, Agent, or Firm* — Oliff PLC

(57) ABSTRACT

Methods for evaluating whether there is a probability that coal will reduce the strength of coke using an apparatus including a stirrer. A degree of entanglement (a–b)/a represented by the heights a and b, or the height a only, is used as an evaluation index for coal, where a height of the semicoke on an inner wall of the container is represented by b, and a height of the semicoke on the stirrer is represented by a. Semicoke formed from heated coal is formed in the container using the degree of entanglement as an evaluation index.

9 Claims, 3 Drawing Sheets

(51) Int. Cl.
    *G01N 11/14*     (2006.01)
    *G01N 33/24*     (2006.01)

(56) References Cited

U.S. PATENT DOCUMENTS

| | | | |
|---|---|---|---|
| 2015/0039242 A1 | 2/2015 | Fukada et al. | |
| 2017/0137716 A1* | 5/2017 | Dohi | ................ C10L 5/04 |

FOREIGN PATENT DOCUMENTS

| | | |
|---|---|---|
| CN | 204656464 U | 9/2015 |
| EP | 2 767 574 A1 | 8/2014 |
| EP | 3 124 574 A1 | 2/2017 |
| EP | 3 263 674 A1 | 1/2018 |
| JP | 2000-304674 A | 11/2000 |
| JP | 2002-294250 A | 10/2002 |
| JP | 2005232349 A | 9/2005 |
| JP | 2011-089002 A | 5/2011 |
| JP | 2015203045 A | 11/2015 |
| KR | 2012-0043952 A | 5/2012 |
| RU | 2 570 875 C1 | 12/2015 |
| RU | 2 675 567 C1 | 12/2018 |
| TW | 201217768 A | 5/2012 |
| WO | 2013/145677 A1 | 10/2013 |
| WO | 2016/024513 A1 | 2/2016 |

OTHER PUBLICATIONS

Jul. 6, 2021 Office Action issued in Taiwanese Patent Application No. 109108099.
Feb. 17, 2022 Extended European Search Report issued in European Patent Application No. 20774444.2.
Mar. 10, 2022 Office Action issued in Russian Patent Application No. 2021127034.
Apr. 21, 2020 International Search Report issued in International Patent Application No. PCT/JP2020/009316.
1 Jan. 3, 2023 Office Action issued in Korean Patent Application No. 10-2021-7028499.
Jun. 6, 2022 Office Action issued in Australian Patent Application No. 2020241658.
Sep. 28, 2022 Office Action issued in Canadian Patent Application No. 3,130,078.
Zhan W., et al. "Cracking phenomenon of lump coal in COREX melting gasifier", Iron and Steel, vol. 48. No. 1, pp. 20-36, Jan. 2013.
Oct. 27, 2023 Office Action issued in Chinese Patent Application No. 202080019357.8.

* cited by examiner

METHOD FOR EVALUATING COAL, METHOD FOR PREPARING COAL BLEND, AND METHOD FOR PRODUCING COKE

TECHNICAL FIELD

This application relates to a method for evaluating coal used as a raw material for metallurgical coke, a method for preparing a coal blend using the evaluating method, and a method for producing coke from a coal blend obtained by the preparing method.

BACKGROUND

Metallurgical coke used as blast furnace feed material to produce molten iron in blast furnaces is preferred to have high strength. This is because coke with low strength is degraded in a blast furnace to reduce the gas permeability of the blast furnace and therefore molten iron cannot be stably produced. Thus, a technique for evaluating coal as a raw material for metallurgical coke is required from the viewpoint of obtaining high strength coke or the viewpoint of not reducing the strength of coke.

Patent Literature 1 describes that coal in a plastic state has a significant influence on the quality of coke during coking process in a coke oven. As described above, in the evaluation of coal, it is important to precisely evaluate properties of coal in a plastic state. As described in Patent Literature 1, a fluidity measurement method using a Gieseler plastometer method specified in JIS-M8801 is known as a method for evaluating the same.

CITATION LIST

Patent Literature

PTL 1: Japanese Unexamined Patent Application Publication No. 2000-304674

SUMMARY

Technical Problem

As described in Patent Literature 1, it is known that there is a problem in that it is uncertain whether the use of fluidity measured with a Gieseler plastometer simulates a phenomenon occurring in an actual coke oven. There is a problem in that estimating the quality of coke using the fluidity of coal measured with a Gieseler plastometer as an index is not sufficient in terms of accuracy. A technique for evaluating coal as a raw material for metallurgical coke using an index other than the fluidity of coal is required.

The disclosed embodiments are intended to solve the above problems and have an object to provide a method for evaluating whether there is a probability that coal intended to be evaluated reduces the strength of coke using an apparatus, such as a Gieseler plastometer hitherto widely known, including a container storing coal and a stirrer insertably placed in the container. Furthermore, the disclosed embodiments have an object to provide a method for preparing a coal blend containing coal evaluated by the method and a method for producing coke by carbonizing a coal blend obtained by the preparing method.

Solution to Problem

In an experiment performed to measure the Gieseler fluidity, the inventors have observed a phenomenon that the shape of heated coal (semicoke) remaining in a container of a Gieseler plastometer after measurement varies depending on coals. The inventors have investigated whether this shape can be used to evaluate coal, leading to the completion of the disclosed embodiments. That is, the disclosed embodiments are as summarized below.

(1) A method for evaluating coal includes using an apparatus including a container storing coal and a stirrer insertably placed in the container. In the method for evaluating coal, a degree of entanglement (a−b)/a represented by a height b of semicoke on an inner wall of the container, the semicoke being formed in the container in such a manner that the stirrer is rotated while the coal stored in the container is being heated, and a height a of the semicoke on the stirrer is used as an evaluation index.

(2) In the method for evaluating coal specified in (1), the apparatus is a Gieseler plastometer and coal in which the degree of entanglement (a−b)/a is 0.20 or more as determined under conditions that a heating temperature of the coal is higher than or equal to a resolidification temperature of the coal is rated poor as coal for metallurgical coke.

(3) A method for evaluating coal includes using an apparatus including a container storing coal and a stirrer insertably placed in the container. In the method for evaluating coal, a height a of semicoke on the stirrer, the semicoke being formed in the container and being entangled with the stirrer in such a manner that the stirrer is rotated while the coal stored in the container is being heated, is used as an evaluation index.

(4) In the method for evaluating coal specified in (3), the apparatus is a Gieseler plastometer and coal in which the height a is 30 mm or more as determined under conditions that a heating temperature of the coal is higher than or equal to a resolidification temperature of the coal is rated poor as coal for metallurgical coke.

(5) A method for preparing a coal blend includes mixing coal rated poor by the method for evaluating coal specified in (2) or (4) with coal different from the coal. In the method for preparing the coal blend, a mass percentage of the coal rated poor in the coal blend is 10% by mass or less.

(6) A method for preparing a coal blend includes mixing coal rated poor by the method for evaluating coal specified in (2) or (4) with coal different from the coal. In the method for preparing the coal blend, a mass percentage of the coal rated poor is identified from a relationship between a strength of coke obtained by carbonizing a plurality of coal blends and the mass percentage of the coal rated poor in the plurality of coal blends, the plurality of coal blends differing with each other in mass percentages of the coal rated poor and the coal different from the coal rated poor, and the identified mass percentage of the coal rated poor such that the strength of coke is greater than or equal to a desired value.

(7) A method for producing coke includes carbonizing a coal blend prepared by the method for preparing a coal blend specified in (5) or (6).

Advantageous Effects

According to the disclosed embodiments, whether there is a probability that coal intended to be evaluated reduces the strength of coke can be grasped. Even in the case of using coal rated poor in the disclosed embodiments in a coal blend used as a source of coke, if the mass percentage of the coal in the coal blend, the mass percentage being capable of suppressing the reduction in strength of coke, is grasped, then an operation producing coke in such a manner that the reduction in strength of coke is suppressed and the usage of the coal is optimized can be achieved. This enables coal previously regarded as unusable to be used. Furthermore, even in the case of using coal rated poor in the disclosed embodiments in a coal blend, coal forming a coal blend capable of producing coke with desired strength and the mass percentage thereof can be identified.

DETAILED DESCRIPTION

The disclosed embodiments provide a method for evaluating coal using the shape of semicoke formed from coal heated with an apparatus including a container storing coal and a stirrer insertably placed in the container as an index. In particular, the method is such that the degree of entanglement (a−b)/a represented by the height b of semicoke on an inner wall of the container and the height a of the semicoke on the stirrer or the height a only is used as an evaluation index for coal.

Figure 1:
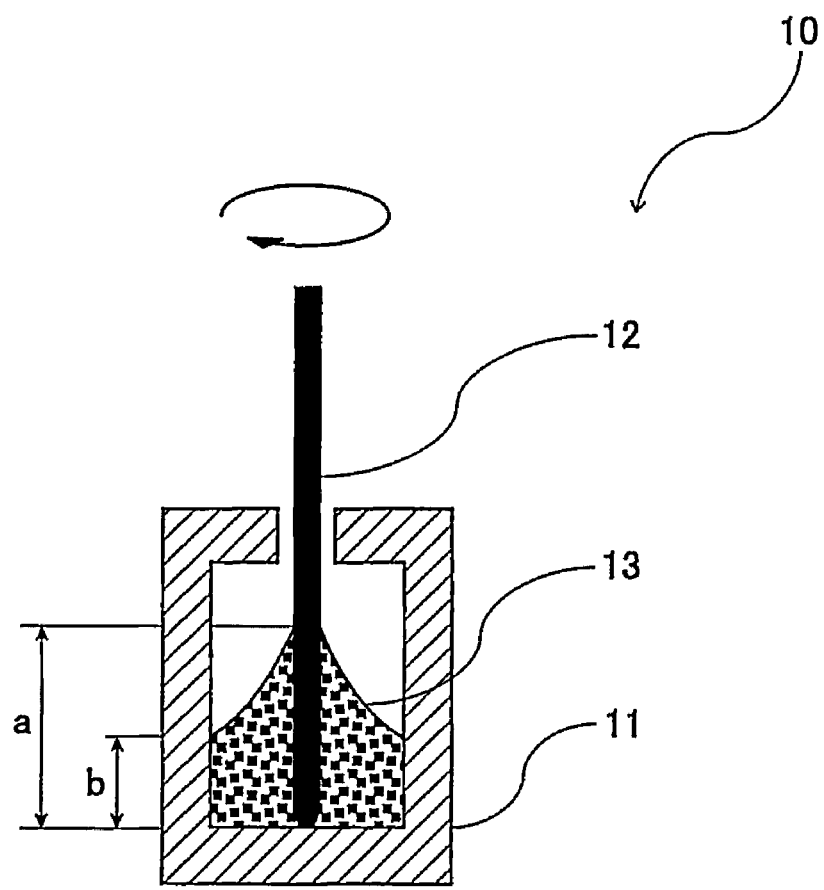
FIG. 1 is a vertical sectional view showing an example of a Gieseler plastometer.

FIG. 1 is a vertical sectional view showing an example of a Gieseler plastometer 10 usable in this embodiment. The Gieseler plastometer 10 includes a container 11 storing coal intended to be evaluated and a stirrer 12 insertably placed in the container 11. The stirrer 12 is equipped with a driving device, which is not shown, and is rotatable. The driving device applies predetermined torque to the stirrer 12 in such a state that the stirrer 12 is inserted in the coal stored in the container 11. Next, heating the container 11 allows the heated coal 13 to be in a plastic state. Since the coal 13 is a viscoelastic body, the coal 13 is deformed and is entangled with the rotating stirrer 12. Force to maintain a shape works on the coal 13 and force to resist rotation exerts on the stirrer 12.

In a fluidity measurement method using a Gieseler plastometer method, the rotational speed of the stirrer 12 is measured in such a state that predetermined torque is applied to the stirrer 12, followed by determining the maximum rotational speed during heating as the Gieseler maximum fluidity MF (ddpm). In some cases, a measurement value is represented by log MF, which is the common logarithm of the Gieseler maximum fluidity MF. Measurement conditions such as the heating temperature of coal and the size of the container 11 are specified in JIS M 8801 and are as described below.

The stirrer 12, which is equipped with a shaft with a diameter of 4.0 mm and four crossbars (a diameter of 1.6 mm and a length of 6.4 mm) perpendicular to the shaft, is inserted into the container 11, which has a depth of 35.0 mm and an inside diameter of 21.4 mm, followed by filling the container with 5 g of coal. Next, the container 11 is dipped in molten metal preheated to 300° C. or 350° C. and heating at a rate of 3° C./minute is continued until the rotation of the stirrer 12 stops. Herein, the distance between the lowest crossbar of the stirrer 12 and the bottom of the container is 1.6 mm and the distance between the crossbars in an axial direction is 3.2 mm. The central two crossbars are located at positions 180 degrees different from each other, the uppermost and lowermost crossbars are also located at positions 180 degrees different from each other, and the central two crossbars and the two uppermost and lowermost crossbars are located at positions 90 degrees different from each other. Conditions specified in ASTM D2639 are similar to conditions specified in JIS M 8801 and therefore a method of ASTM may be used. In the case not using a Gieseler plastometer, a stirrer with a diameter that is 5% to 60% of the inside diameter of a container storing coal is preferably used. The stirrer is preferably equipped with crossbars. Even if the stirrer is equipped with no crossbars, the entanglement of softened or molten coal with the stirrer occurs.

Coal is softened and melted by heating to exhibit fluidity and molten coal is resolidified by further heating. Therefore, after measurement under the above-mentioned conditions, coal heated under conditions that the heating temperature is higher than or equal to the resolidification temperature of the coal is converted into semicoke 13, which is stored in the container 11. Coal and semicoke are plastic bodies. Therefore, after the Gieseler fluidity is measured, the coal (semicoke) 13 in heating and stirring is in contact with an inner wall of the container 11, is pulled with the stirrer 12, and is held in such a form that the coal (semicoke) 13 is entangled with the stirrer 12. Thus, in most brands of coal, as shown in FIG. 1, the height a of the semicoke 13 in contact with the stirrer 12 from the bottom of the container 11 is greatest and the height b of the semicoke 13 in contact with the inner wall of the container 11 from the bottom is least. The behavior of softened or molten coal is known as the Weissenberg effect.

The heights a and b can be measured by disassembling the container after measurement. An image of the shape of semicoke can be obtained by scanning the container 11 with a microfocus X-ray CT system after the measurement of fluidity. The heights a and b can be measured from the image. The microfocus X-ray CT system is, for example, XTH320LC manufactured by Nikon Corporation, phoenix v|tome|xm300 manufactured by GE Sensing & Inspection Technologies Co., Ltd., or the like. Since there is little difference depending to a position in a circumferential direction of the container for the height a and the height b, it is usually sufficient to measure the shape of a cross section. If there is a difference depending to a position therebetween, the height is measured in a plurality of cross sections and the average of the measurements may be used as the value of the height a or b.

The shape of semicoke after the measurement of Gieseler fluidity varies depending on coal. The inventors have conceived that the height of semicoke in a container serves as an index showing the influence on the strength of coke, have investigated the relationship between the degree of entanglement (a−b)/a represented by the height of semicoke in a container and the strength of coke, and have found that the strength of coke obtained from the coal can be estimated from the degree of entanglement. The inventors have found that even if the height a of semicoke on a stirrer is used instead of the degree of entanglement, the strength of coke can be estimated as is the case with the degree of entanglement.

In a plastic state, coal with a high degree of entanglement and coal in which the height a of semicoke on a stirrer is large have excessively high dilatation, are likely to cause a defect structure in heated coke, and are supposed to have a negative influence on the strength of coke. Thus, in this embodiment, when the degree of entanglement or height a of coal is greater than or equal to a predetermined value, the coal is evaluated as poor. For example, under measurement conditions of a Gieseler plastometer specified in JIS or the like, coal with a degree of entanglement of 0.20 or more or coal with a height a of 30 mm or more is rated poor as coal for metallurgical coke. As the degree of entanglement and the height a are larger, the dilatation is higher, which can be judged to have a negative influence on the strength of coke. Therefore, for the degree of entanglement and the height a, no upper limit for evaluating coal needs to be set. Incidentally, for both the degree of entanglement and the height a, measurement values are limited by the size of a container storing sample coal. Thus, measurement is preferably performed using a container capable of measuring a degree of entanglement of 0.20 or more or a height a of 30 mm or more.

The semicoke 13 is not at all in contact with the inner wall (side wall) of the container 11 depending on the brand of coal in some cases because all the semicoke 13 is pulled by the stirrer 12. Even in this case, coal is supposed to have excessively high dilatation; hence, there is no harm in evaluating coal by calculating the degree of entanglement and the degree of entanglement may be calculated to be 1 by substituting 0 for b.

In an operation preparing a coal blend by mixing coal rated poor with coal different from the coal, the reduction in strength of coke produced by carbonizing the coal blend can be suppressed by suppressing the mass percentage of the coal rated poor in the coal blend. In this embodiment, the coal blend is prepared such that the mass percentage of the coal rated poor in the coal blend is, for example, 10% by mass or less. This enables the reduction in strength of coke to be suppressed in most operations.

Upon performing an operation, a plurality of coal blends differing in the mass percentages of coal rated poor and coal different from the coal are prepared and the relationship between the strength of coke obtained by carbonizing each coal blend and the mass percentage of coal rated poor is obtained in advance. This enables the mass percentage of the coal rated poor to be identified from the relationship therebetween such that the strength of coke is greater than or equal to a desired value in the operation and allows a coal blend to be prepared such that the mass percentage of the coal rated poor in the coal blend is less than or equal to the identified mass percentage. As a result, a coal blend can be prepared using coal rated poor such that the strength of coke is greater than or equal to a desired degree.

A coal blend may be prepared in such a manner that the relationship between the strength of coke and the mass percentage of coal rated poor is obtained in advance and the mass percentage of the coal rated poor is identified from the relationship obtained in advance such that the strength of coke is greater than or equal to a desired value. That is, an entity that prepares a coal blend may be different from an entity that obtains the relationship. Herein, the term "entity" refers to a person or organization that performs the act. Coke with a strength greater than or equal to a desired value can be produced in such a manner that coke is produced by carbonizing a coal blend prepared as described above in a coke oven or the like.

<Experiments>

Figure 2:
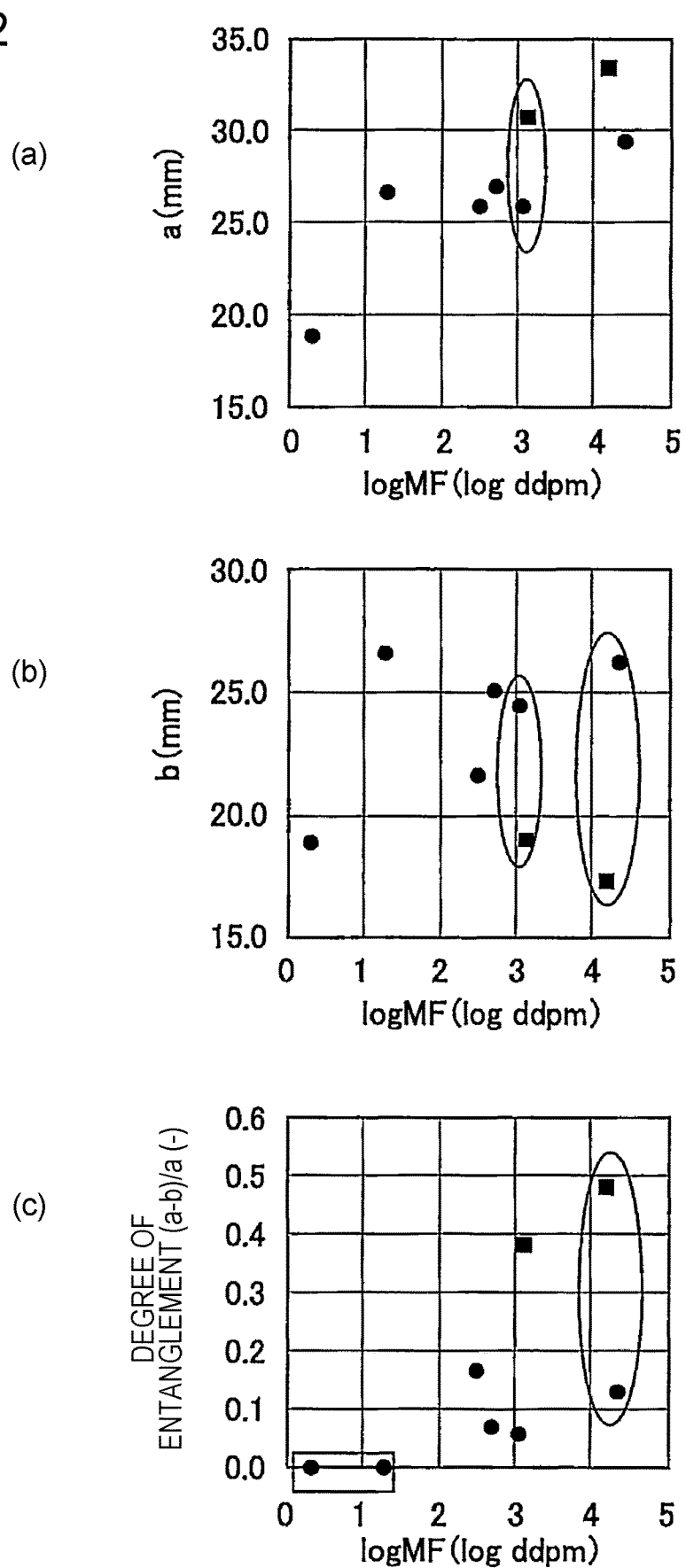
FIG. 2 includes graphs showing correlations between the height a of semicoke on a stirrer of a Gieseler plastometer, the height b of semicoke on an inner wall of a container, the degree of entanglement (a−b)/a, and the Gieseler maximum fluidity log MF.

Next, the following experiments are described: experiments in which various coals with different properties were prepared and in which correlations between the height a of semicoke on a stirrer, the height b of semicoke on an inner wall of a container, the degree of entanglement (a−b)/a, and the Gieseler maximum fluidity log MF were investigated. FIG. 2 includes graphs showing correlations between the height a of semicoke on a stirrer of a Gieseler plastometer, the height b of semicoke on an inner wall of a container, the degree of entanglement (a−b)/a, and the Gieseler maximum fluidity log MF. FIG. 2(a) is a graph showing the relationship between the height a on the stirrer and log MF. FIG. 2(b) is a graph showing the relationship between the height b on the inner wall of the container and log MF. FIG. 2(c) is a graph showing the relationship between the degree of entanglement (a−b)/a and log MF.

According to the graph of FIG. 2(a), the height a increases with the increase of log MF and this can be read as if a positive relationship holds between log MF and the height a. However, as indicated by enclosure in ○ in the graph, points that differ in the value of a even though log MF is almost the same, about 3, are confirmed. Thus, it is hard to say that a positive relationship holds between log MF and the height a.

According to the graph of FIG. 2(b), data varies and it cannot be read that a relationship holds between log MF and the height b. As is the case with a in FIG. 2(a), a plurality of points that are almost identical in log MF and that differ in the value of b are confirmed. Thus, it cannot be said that a relationship holds between log MF and the height b.

As indicated by rectangular enclosure in the graph of FIG. 2(c), two points that differ in log MF and that are identical in the degree of entanglement, which is 0, are confirmed. As indicated by circular enclosure in the graph, the degree of entanglement differs even though log MF is almost the same. From these results, it cannot be said that a relationship holds between log MF and the degree of entanglement.

In view of the above results, it cannot be said that the degree of entanglement, which is an evaluation index used in this embodiment, correlates with the Gieseler maximum fluidity and it can be said that the degree of entanglement is an evaluation index different from the Gieseler maximum fluidity.

Black square plots in FIG. 2(c) represent two types of coal in which the degree of entanglement (a−b)/a is 0.2 or more. It was recognized that the two types of coal had a height a of 30 mm or more and coal with a high degree of entanglement tended to have a large height a.

Examples

In order to investigate the influence of the degree of entanglement (a−b)/a and the height a on the strength of coke, a carbonization test was performed using Coals A to F. Properties of the coals used are shown in Table 1. The carbonization test was such that coke was produced in such a manner that an electric furnace capable of simulating carbonization conditions of a coke oven was used and a coal blend charged into the furnace at a bulk density of coal charge of 750 kg/dry-coal was carbonized at 1,050° C. for six hours. Properties and the degree of entanglement (a−b)/a of the prepared coals are shown in Table 1.

TABLE 1

| Item Unit | Ash % | Volatile matter % | Ro % | TI % | log MF log ddpm | Height a mm | Height b mm | Degree of entanglement — |
|---|---|---|---|---|---|---|---|---|
| Coal A | 7.8 | 35.7 | 0.87 | 14.6 | 4.19 | 33.4 | 17.3 | 0.48 |
| Coal B | 6.2 | 30.6 | 1.07 | 11.5 | 3.12 | 30.8 | 19.0 | 0.38 |
| Coal C | 6.8 | 42.1 | 0.62 | 20.2 | 4.35 | 29.4 | 26.0 | 0.12 |
| Coal D | 8.6 | 32.0 | 1.03 | 35.5 | 3.05 | 25.9 | 24.4 | 0.06 |
| Coal E | 8.1 | 34.1 | 0.95 | 29.0 | 2.70 | 27.0 | 25.1 | 0.07 |
| Coal F | 7.3 | 33.8 | 0.93 | 33.9 | 2.49 | 26.0 | 21.6 | 0.17 |

In Table 1, "Ash" and "Volatile matter" are values (mass percent on a dry basis) measured by a method for proximate analysis in JIS M 8812. "Ro" is the mean maximum reflectance of vitrinite of coal in JIS M 8816 and "TI" is the total inert (volume percent) in coal maceral analysis as calculated on the basis of Parr's formula described in a method for measuring coal macerals in JIS M 8816 and an explanation thereof. "log MF" is the value of the common logarithm log of the maximum fluidity MF measured by a fluidity measurement method using a Gieseler plastometer method specified in JIS M 8801. As shown in Table 1, Coals A to F have different properties.

In Table 1, "Degree of entanglement" is the value of the degree of entanglement (a–b)/a calculated using the heights a and b measured by a method for evaluating coal according to this embodiment using the Gieseler plastometer shown in FIG. 1. The heights a and b were actually measured from an image of the cross-sectional shape of semicoke that was obtained by scanning the container 11 with an X-ray CT system, XTH320LC, manufactured by Nikon Corporation.

What is noteworthy in Table 1 is that Coals A and B have a height a of 30 mm or more and a degree of entanglement of 0.20 or more. Coal F can be regarded as standard coal in the technical field of producing metallurgical coke from coal in view of properties such as Ro and log MF shown in Table 1.

In this example, furthermore, coke was produced by carbonizing a coal mixture, composed of two types of coal, obtained by mixing each of Coals A to E with Coal F at a ratio of 2:8. The strength of obtained coke is shown in Table 2.

TABLE 2

| Item | Strength of coke |
|---|---|
| Unit | DI 150/15 |
| Coal mixture AF | 84.0 |
| Coal mixtute BF | 83.6 |
| Coal mixture CF | 84.6 |
| Coal mixture DF | 84.3 |
| Coal mixture EF | 84.7 |

As the strength of coke, the drum strength DI 150/15, which is mass ratio×100, the mass ratio being a ratio of the mass of coke with a particle size of 15 mm or more after rotation to the mass of coke before rotation, was determined in such a manner that the mass percentage of coke with a particle size of 15 mm or more was measured after a drum tester charged with a predetermined amount of coke was rotated at 15 rpm 150 times on the basis of a drum strength test method of JIS K 2151. In Table 2, the strength of coke obtained from a coal mixture composed of two types of coal is described.

As is clear from Table 2, coke obtained from a coal mixture of Coal A or B and Coal F has strength lower than that of the case of mixing Coals C, D, and E with Coal F. Coals A and B both have a degree of entanglement (a–b)/a of 0.20 or more or a height a of 30 mm or more. This allows coal with a degree of entanglement (a–b)/a of 0.20 or more to be rated poor as coking coal for cokemaking. Likewise, coal with a height a of 30 mm or more can be rated poor as coking coal for cokemaking.

Next, the limit of the blending ratio of coal rated poor as coking coal for cokemaking was investigated.

A coal mixture of Coals A and C and a plurality of brands of coal was prepared and five types of coal blends were prepared by varying the blending ratios of Coals A and C such that the blending ratio of the coal mixture was 80% by mass and the sum of the blending ratios of Coals A and C was 20% by mass. Coke was produced in such a manner that an electric furnace capable of simulating carbonization conditions of a coke oven was used and the coal blends were charged into the furnace at a bulk density of coal charge of 750 kg/dry basis and were carbonized at 1,050° C. for six hours. Properties of the prepared coals and coal mixture are shown in Table 3. Herein, for the ash, volatile matter, Ro, TI, and log MF of the coal mixture, the average properties are shown and, for the height a and degree of entanglement thereof, values actually measured using a Gieseler plastometer are shown.

TABLE 3

| Item Unit | Ash % | Volatile matter % | Ro % | TI % | MF log ddpm | Height a mm | Degree of entanglement — |
|---|---|---|---|---|---|---|---|
| Coal A | 7.8 | 35.7 | 0.87 | 14.6 | 4.19 | 33 | 0.48 |
| Coal C | 6.8 | 42.1 | 0.62 | 20.2 | 4.35 | 29 | 0.12 |
| Coal mixture | 9.2 | 28.5 | 1.16 | 32.5 | 2.00 | 26 | 0.09 |

Figure 3:
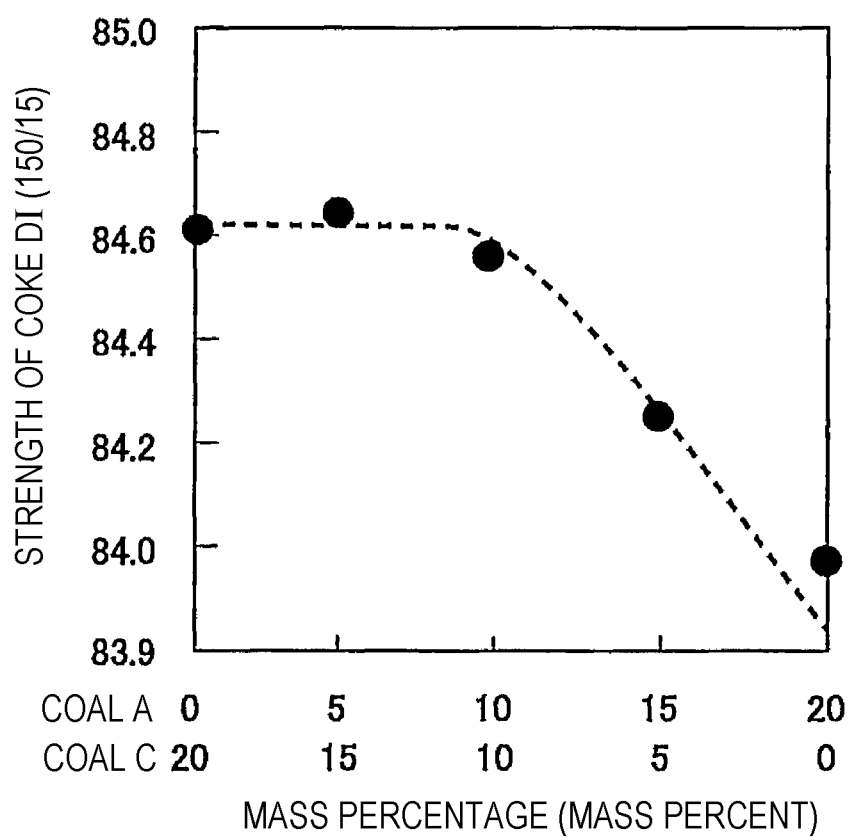
FIG. 3 is a graph showing the relationship between the strength DI (150/15) of coke obtained from a coal blend in an example and the mass percentage of coal in the coal blend.

FIG. 3 is a graph showing the relationship between the strength DI (150/15) of coke and the mass percentages of Coals A and C in each coal blend used as a source of coke. The blending ratios of Coals A and C are clear from the mass percentage plotted in FIG. 3. According to FIG. 3, although Coals A and C have relatively similar properties, the strength of coke in the case of blending 20% by mass of Coal A is lower than the strength of coke in the case of blending 20% by mass of Coal C. That is, it can be confirmed from this test that Coal A is poor as coal for metallurgical coke.

From the graph of FIG. 3, for the mass percentage of Coal A, which is rated poor, and the strength of coke, a correlation that the reduction in mass percentage of Coal A increases the strength of coke can be read. That is, suppressing the mass percentage of Coal A allows the strength of coke to be maintained at a high level. Furthermore, from the graph of FIG. 3, it is clear that suppressing the mass percentage of Coal A in a coal blend to 10% by mass or less enables the reduction in strength of coke to be suppressed and enables the strength of coke to be maintained at a high level. The negative influence of coal rated poor by the method for evaluating coal according to this embodiment on the strength of coke is smaller as the blending ratio thereof is lower. Therefore, the lower limit of the blending ratio of coal rated poor is 0% by mass.

If the desired strength of coke is set to about 84.6 in terms of the drum strength DI (150/15), it can be identified from the graph of FIG. 3 that the mass percentage of Coal A with which the strength of coke can be maintained at a high level is 10% by mass or less. Thus, the production of coke with desired strength can be achieved in such a manner that a coal blend is prepared such that the mass percentage of Coal A is 10% by mass or less, followed by producing coke.

In this example, the following relationship is obtained: the relationship between the strength of coke obtained by carbonizing a plurality of coal blends differing in the mass percentages of coal (which is hereinafter referred to as "poor coal" and is Coal A in this example) rated poor in terms of (a−b)/a or the height a and coal different from the poor coal and the mass percentage of the poor coal. In this example, an example of the following method is shown: a method for preparing a coal blend such that the mass percentage of poor coal in which the strength of coke is greater than or equal to a desired value is identified on the basis of the above relationship and the mass percentage of the poor coal is less than or equal to the identified mass percentage.

From the above examples, it has been confirmed that whether the strength of coke obtained from a coal blend containing coal rated poor in terms of the degree of entanglement (a−b)/a and the height a, which are evaluation indexes of the disclosed embodiments, decreases can be grasped. It has been confirmed that the mass percentage of coal rated poor in a coal blend and the mass percentage with which the reduction in strength of coke is suppressed can be grasped. Furthermore, it has been confirmed that in the case of performing an operation producing coke using coal rated poor, the production of coke with desired strength can be achieved in such a manner that coal forming a coal blend capable of producing coke with desired strength and the mass percentage thereof are identified and coke is produced using a coal blend prepared such that coal and the mass percentage thereof are as identified.

The invention claimed is:

1. A method for preparing a coal blend, the method comprising:
    evaluating coal using an apparatus including a container storing coal and a stirrer insertably placed in the container, by:
        heating the container while rotating the stirrer in order to heat the coal,
        determining a degree of entanglement (a−b)/a represented by a height b of semicoke on an inner wall of the container, and a height a of the semicoke on the stirrer as an evaluation index, and
        forming the semicoke using the evaluation index, wherein coal in which the degree of entanglement (a−b)/a is 0.20 or more as determined under conditions that a heating temperature of the coal is higher than or equal to a resolidification temperature of the coal is rated poor as coal for metallurgical coke; and
    mixing coal rated poor by the evaluating with coal different from the coal rated poor, wherein a mass percentage of the coal rated poor in the coal blend is 10% by mass or less.

2. The method according to claim 1, wherein the apparatus is a Gieseler plastometer.

3. A The method according to claim 1, wherein
the mass percentage of the coal rated poor is identified from (i) a relationship between a strength of coke obtained by carbonizing a plurality of coal blends and the mass percentage of the coal rated poor in the plurality of coal blends, the plurality of coal blends differing with each other in mass percentages of the coal rated poor and the coal different from the coal rated poor, and (ii) the identified mass percentage of the coal rated poor such that the strength of coke is greater than or equal to a desired value, and
the coal blend is prepared such that the mass percentage of the coal rated poor is less than or equal to the identified mass percentage.

4. A method for producing coke, the method comprising carbonizing the coal blend prepared by the method according to claim 1.

5. A method for producing coke, the method comprising carbonizing the coal blend prepared by the method according to claim 3.

6. A method for preparing a coal blend, the method comprising:
    evaluating coal using an apparatus including a container storing coal and a stirrer insertably placed in the container, by:
        heating the container while rotating the stirrer in order to heat the coal, wherein the container has a depth of 35.0 mm and an inside diameter of 21.4 mm,
        determining a height a of semicoke entangled with and on the stirrer as an evaluation index for evaluating whether there is a probability that the coal evaluated reduces a strength of coke obtained from a coal blend containing the coal, and
        forming the semicoke using the evaluation index, wherein coal in which the height a is 30 mm or more as determined under conditions that a heating temperature of the coal is higher than or equal to a resolidification temperature of the coal is rated poor as coal for metallurgical coke, and the height a is measured from an image of a cross-sectional shape of the coal obtained by scanning the container with an X-ray CT system; and
    mixing coal rated poor by the evaluating with coal different from the coal rated poor, wherein a mass percentage of the coal rated poor in the coal blend is 10% by mass or less.

7. The method according to claim 6, wherein the apparatus is a Gieseler plastometer.

8. The method according to claim 6, wherein
the mass percentage of the coal rated poor is identified from (i) a relationship between a strength of coke obtained by carbonizing a plurality of coal blends and the mass percentage of the coal rated poor in the plurality of coal blends, the plurality of coal blends differing with each other in mass percentages of the coal rated poor and the coal different from the coal rated poor, and (ii) the identified mass percentage of the coal rated poor such that the strength of coke is greater than or equal to a desired value, and
the coal blend is prepared such that the mass percentage of the coal rated poor is less than or equal to the identified mass percentage.

9. A method for producing coke, the method comprising carbonizing the coal blend prepared by the method according to claim 8.

* * * * *